US00PP19999P2

(12) United States Plant Patent
Unger

(10) Patent No.: US PP19,999 P2
(45) Date of Patent: May 19, 2009

(54) ***GLECHOMA* PLANT NAMED 'RAPUNZEL'**

(50) Latin Name: *Glechoma variegata*
Varietal Denomination: RAPUNZEL

(76) Inventor: Christiaan Unger, Robert Koch Strasse 7, 67511 Worms (DE)

( * ) Notice: Subject to any disclaimer, the term of this patent is extended or adjusted under 35 U.S.C. 154(b) by 29 days.

(21) Appl. No.: 11/824,110

(22) Filed: Jun. 30, 2007

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

U.S. PATENT DOCUMENTS

PP17,683 P3 * 5/2007 Plt. ..... Plt./263.1

* cited by examiner

*Primary Examiner*—Wendy C. Haas
(74) *Attorney, Agent, or Firm*—Mark P. Bourgeois

(57) ABSTRACT

A new and distinct *Glechoma* plant cultivar is disclosed, characterized by a low, compact spreading plant habit; and small, yellow-gold edged, variegated leaves.

1 Drawing Sheet

Latin name of the genus and species: *Glechoma variegata.*
Variety denomination: 'Rapunzel'.

BACKGROUND OF THE INVENTION

The new cultivar 'Rapunzel' is a product of a naturally occurring whole plant mutation. The new cultivar was discovered and selected as a single plant by Christiaan Unger in October 2003 in a cultivated area of Rheinfelden, Germany. 'Rapunzel' was discovered in a field of *Glechoma* plants in an outdoor area.

Asexual reproduction of the new cultivar 'Rapunzel' by vegetative cuttings was performed in Oxnard, Calif., and has shown that the unique features of this new cultivar are stable and reproduced true to type on successive generations.

SUMMARY OF THE INVENTION

The cultivar 'Rapunzel' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Rapunzel.' These characteristics in combination distinguish 'Rapunzel' as a new and distinct *Glechoma* cultivar:

1. Low, compact spreading plant habit; and
2. Small, yellow-gold edged, variegated leaves.

Plants of the new cultivar differ from plants of the parent selections in growth habit and size. The leaves are also much smaller than the unpatented parent variety.

In comparison to the commercially available variety 'Dappled Light' (U.S. Plant Pat. No. 17,683), 'Rapunzel' a taller and has a more widely spreading plant habit. Additionally, the foliage of 'Rapunzel' is a much lighter, truer green with yellow-gold margins. Finally, no flowering has ever been observed in this variety.

BRIEF DESCRIPTION OF THE PHOTOGRAPH

The drawing illustrates in full color a typical plant of 'Rapunzel' grown in an outdoor garden. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'Rapunzel' plants grown in Oxnard, Calif. during the months of January through June in an outdoor garden. The growing temperature ranged from 12° C. to 15° C. at night to 12° C. to 20° C. during the day.

Botanical classification: *Glechoma* cultivar 'Rapunzel.'
Commercial classification: Ground ivy.

PROPAGATION

Time to initiate roots: 8 to 10 days at 20° C.
Time to develop roots: 12 to 14 days at 20° C.
Root description: Fine, fibrous, white in color.
Rooting habit: Freely branching.

PLANT

Growth habit: Low and outwardly spreading annual.
Growth rate: Moderate.
Plant height: About 25 cm.
Plant spread: About 81 cm.
Branching habit: Freely branching.
Number of lateral branches: Variable; average of 7.
Length of lateral branches: About 23 cm.
Stem length: About 14 cm.
Stem diameter: About 0.1 cm.
Strength: Moderate.
Aspect: Initially upright then outwardly spreading.
Texture: Lightly pubescent.

Color: Near Yellow-Green 145A.
Age of plant described: Approximately 138 days.

FOLIAGE

Arrangement: Opposite; simple.
Number of leaves per stem: 4.
Length: About 1.1 cm.
Width: About 1.6 cm.
Shape: Reniform.
Apex: Obcordate.
Base: Cordate.
Margin: Crenate.
Texture:
*Upper surface.*—Smooth.
*Lower surface.*—Smooth.
Venation pattern: Palmate toward the base, becomes reticulate toward the margin of the leaf.
Color:
*Developing foliage on the upper surface.*—Towards the margins: Near Yellow-Green 154D. Center: Near Green 143B.
*Developing foliage on the lower surface.*—Margin: Near Yellow-Green 154D. Center: Near Green 143B.
*Fully expanded foliage on the upper surface.*—Margin: Near Yellow-White 158B with shades of Greyed-Red 179C. Center: Near Green 143C.
*Fully expanded foliage on the lower surface.*—Margin: Near Yellow-White 158B. Center: Near Green 143D.
Petiole length: About 6 cm.
Petiole diameter: About 0.1 cm.
Petiole color:
*Towards the apex.*—Near Yellow-Green 145C.
*Towards the base.*—Near Yellow-Green 145C.
Flower description: Flower development has not been observed.

OTHER CHARACTERISTICS

Disease resistance: Neither resistance nor susceptibility to diseases or pests has been observed in this variety.
Drought tolerance/cold tolerance: Plants of the new have been observed to have no drought tolerance and is hardy to 12 C.
Fruit/seed production: Commercially, this plant is not used or observed in a stage where seeds would be produced. Therefore, seed production has not been observed.

What is claimed is:

1. A new and distinct cultivar of *Glechoma* plant named 'Rapunzel' as herein illustrated and described.

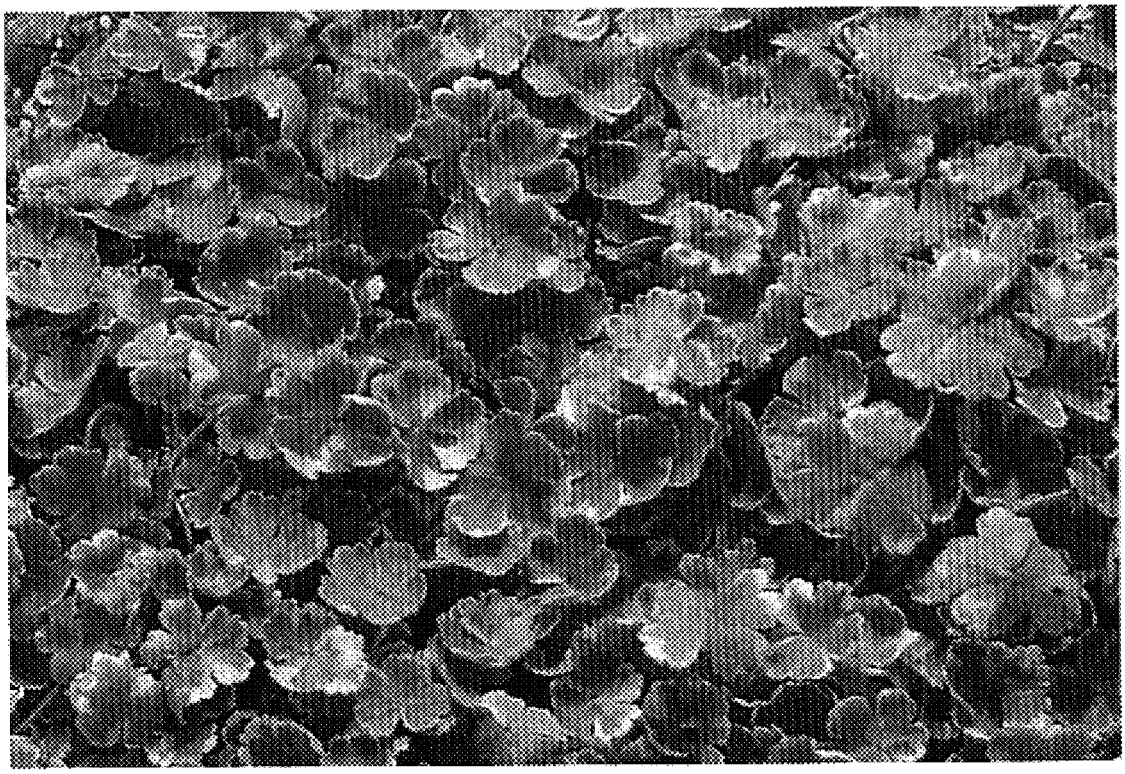

* * * * *